United States Patent
Baumberger et al.

(10) Patent No.: US 10,600,015 B2
(45) Date of Patent: Mar. 24, 2020

(54) CONTEXT-AWARE USER INTERFACE FOR INTEGRATED OPERATING ROOM

(71) Applicant: Karl Storz SE & Co. KG, Tuttlingen (DE)

(72) Inventors: Juri Baumberger, Goleta, CA (US); Timothy Rutland, Santa Barbara, CA (US); Ted Applebaum, Santa Barbara, CA (US); Matteo Contolini, Santa Barbara, CA (US)

(73) Assignee: Karl Storz SE & Co. KG, Tuttlingen (DE)

( * ) Notice: Subject to any disclaimer, the term of this patent is extended or adjusted under 35 U.S.C. 154(b) by 1030 days.

(21) Appl. No.: 14/748,759

(22) Filed: Jun. 24, 2015

(65) Prior Publication Data
US 2016/0378939 A1    Dec. 29, 2016

(51) Int. Cl.
*G06Q 10/06* (2012.01)
*G06Q 50/22* (2018.01)
*G16H 40/20* (2018.01)
*G16H 40/40* (2018.01)
*G16H 20/40* (2018.01)

(52) U.S. Cl.
CPC .  *G06Q 10/0633* (2013.01); *G06Q 10/063114* (2013.01); *G06Q 50/22* (2013.01); *G16H 20/40* (2018.01); *G16H 40/20* (2018.01); *G16H 40/40* (2018.01)

(58) Field of Classification Search
None
See application file for complete search history.

(56) References Cited

U.S. PATENT DOCUMENTS

| 5,692,125 | A  | 11/1997 | Schloss et al. |
| 6,714,913 | B2 | 3/2004  | Brandt et al.  |
| 7,274,290 | B2 | 9/2007  | Morita et al.  |
| 7,310,607 | B2 | 12/2007 | Brandt et al.  |
| 7,371,068 | B2 | 5/2008  | Lloyd et al.   |
| 7,443,303 | B2 | 10/2008 | Spear et al.   |
| 7,447,644 | B2 | 11/2008 | Brandt et al.  |

(Continued)

FOREIGN PATENT DOCUMENTS

| EP | 1769771 A1 | 4/2007  |
| EP | 2945087 A2 | 11/2015 |

(Continued)

OTHER PUBLICATIONS

Florent Lalys et al., Automatic knowledge-based recognition of low-level tasks in ophthalmological procedures, International Journal of Computer Assisted Radiology and Surgery, 2013, 8 (1), pp. 39-49 (2 page abstract).

(Continued)

*Primary Examiner* — Michael Tomaszewski
*Assistant Examiner* — Jay M. Patel
(74) *Attorney, Agent, or Firm* — Whitmyer IP Group LLC

(57) ABSTRACT

A system and method for managing workflow of a medical procedure, including a control and at least one detector such as a sensor, where the control interprets a user input to control the workflow of the medical procedure. The system and method include multiple input modalities and hazard mitigation measures to control the medical procedure and/or control various medical devices in an operating room.

28 Claims, 11 Drawing Sheets

(56) References Cited

U.S. PATENT DOCUMENTS

| | | |
|---|---|---|
| 7,533,353 B2 | 5/2009 | Dvorak et al. |
| 8,313,432 B2 | 11/2012 | Chiu et al. |
| 8,355,928 B2 | 1/2013 | Spahn |
| 8,411,034 B2 | 4/2013 | Boillot et al. |
| 10,034,979 B2* | 7/2018 | Bechtel ............... A61B 5/7275 |
| 2005/0128184 A1 | 6/2005 | McGreevy |
| 2006/0171574 A1* | 8/2006 | DelMonego ........... G16H 40/63 382/128 |
| 2006/0183972 A1* | 8/2006 | Tashiro ............. A61B 1/00041 600/101 |
| 2006/0282302 A1 | 12/2006 | Hussain |
| 2007/0118400 A1 | 5/2007 | Morita et al. |
| 2008/0062280 A1* | 3/2008 | Wang ................... G06F 19/321 348/231.99 |
| 2008/0077408 A1* | 3/2008 | Wang ................... G10L 15/265 704/275 |
| 2008/0083414 A1 | 4/2008 | Messerges |
| 2008/0086035 A1 | 4/2008 | Messerges et al. |
| 2008/0104547 A1 | 5/2008 | Morita et al. |
| 2008/0114212 A1 | 5/2008 | Messerges |
| 2008/0114214 A1 | 5/2008 | Messerges |
| 2008/0114226 A1 | 5/2008 | Music et al. |
| 2008/0164998 A1 | 7/2008 | Scherpbier et al. |
| 2008/0253519 A1 | 10/2008 | Bonfiglio et al. |
| 2009/0021475 A1 | 1/2009 | Steinle et al. |
| 2009/0030695 A1* | 1/2009 | Wang ............................ 704/275 |
| 2009/0125840 A1* | 5/2009 | Squilla ................ G06F 19/3481 715/810 |
| 2010/0022849 A1 | 1/2010 | Franz et al. |
| 2012/0229383 A1 | 9/2012 | Hamilton et al. |
| 2013/0093829 A1* | 4/2013 | Rosenblatt ............... G09B 5/00 348/14.01 |
| 2013/0179162 A1 | 7/2013 | Merschon et al. |
| 2013/0204428 A1 | 8/2013 | Steinle et al. |
| 2013/0225999 A1 | 8/2013 | Banjanin et al. |
| 2014/0006049 A1* | 1/2014 | Moctezuma de la Barrera .......... G06Q 10/06316 705/2 |
| 2014/0081659 A1* | 3/2014 | Nawana .................. G16Z 99/00 705/3 |
| 2014/0088990 A1* | 3/2014 | Nawana .................. G16Z 99/00 705/2 |
| 2014/0181716 A1* | 6/2014 | Merritt ................. A61B 5/0066 715/771 |
| 2014/0204190 A1* | 7/2014 | Rosenblatt, III ......... G09B 5/00 348/77 |
| 2014/0213845 A1* | 7/2014 | Bechtel ................. A61M 5/142 600/28 |
| 2014/0263633 A1* | 9/2014 | Schmucker ............ G06Q 50/22 235/385 |
| 2015/0332196 A1* | 11/2015 | Stiller .............. G06Q 10/06316 705/2 |

FOREIGN PATENT DOCUMENTS

| | | |
|---|---|---|
| WO | 2011060185 A1 | 5/2011 |
| WO | 2011060187 A1 | 5/2011 |
| WO | 2012044334 A2 | 4/2012 |
| WO | 2012129669 A1 | 10/2012 |
| WO | 2012174539 A1 | 12/2012 |
| WO | 2013038293 A1 | 3/2013 |
| WO | 2014134196 A1 | 9/2014 |

OTHER PUBLICATIONS

N. Padoy et al., Statistical Modeling and Recognition of Surgical Workflow Medical/Image Analysis (2010), vol. 16, Issue 3, Apr. 2012 (published online Dec. 2010), pp. 632-641.

Houliston BR et al.(2011) TADAA: towards automated detection of anesthetic activity, Methods Inf Med 50(5): 464-471; (1 page abstract).

Extended European Search Report Application No. 16175741.4 Completed: Nov. 8, 2016; dated Nov. 15, 2016 11 Pages.

European Office Action Application No. 16175741.4 Completed: Sep. 17, 2019 11 Pages.

* cited by examiner

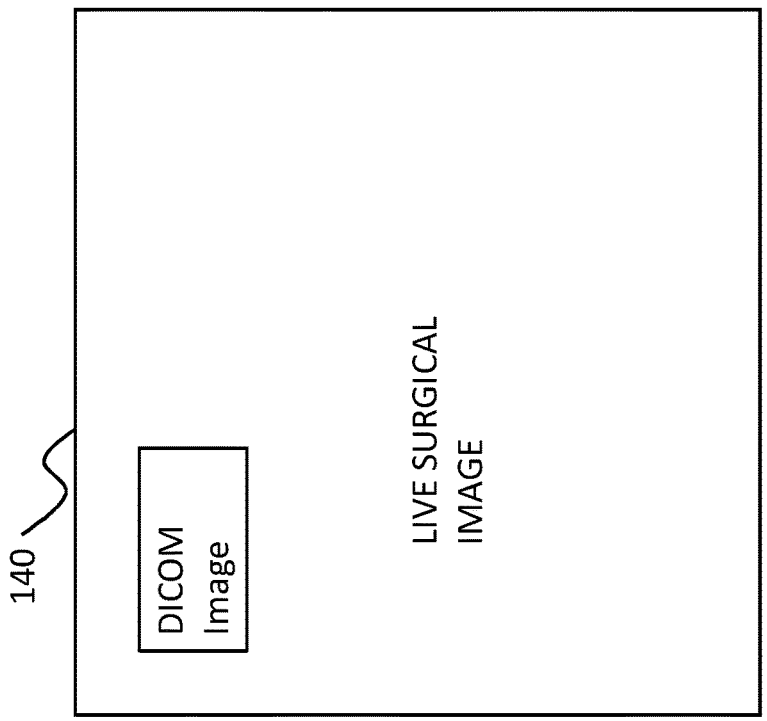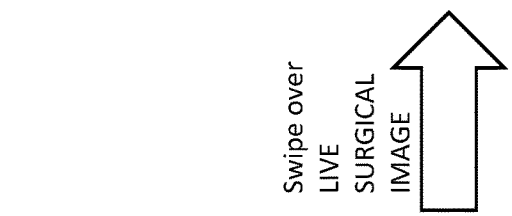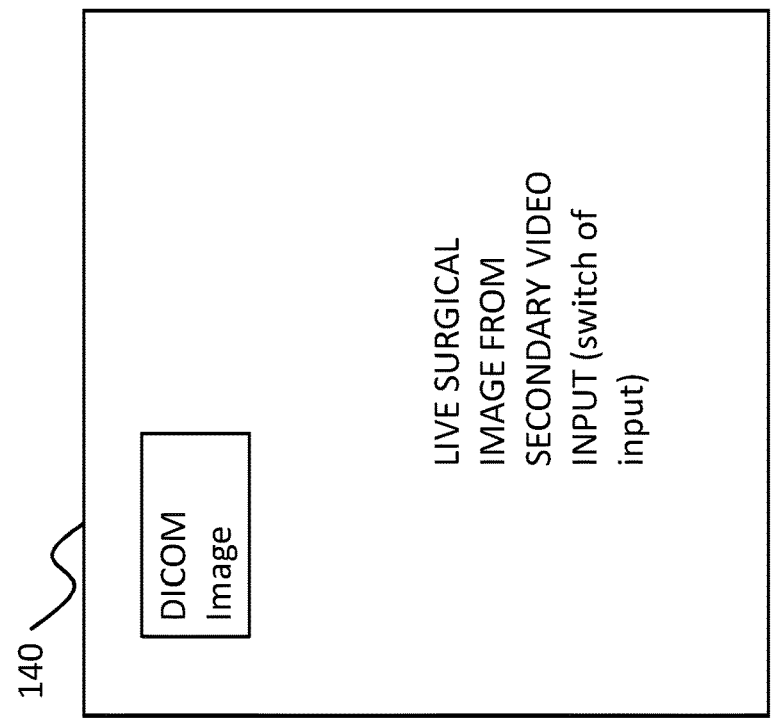
FIG. 7a

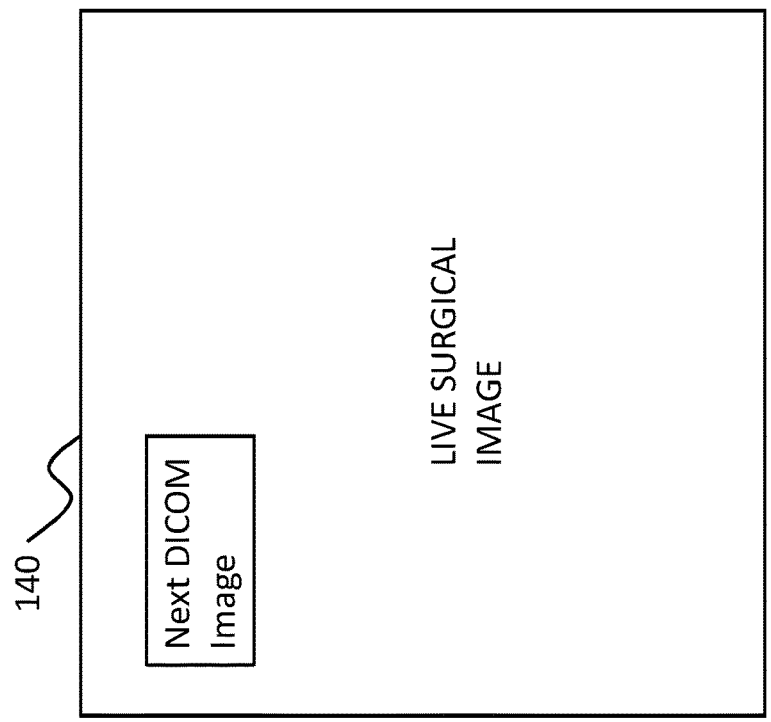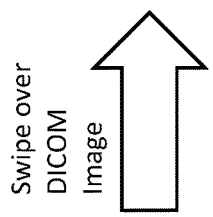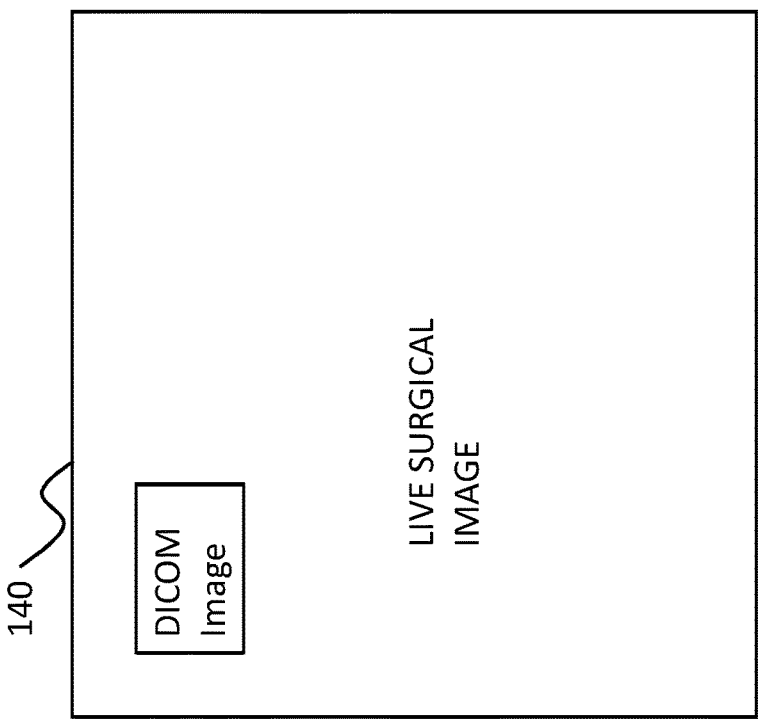
FIG. 7b

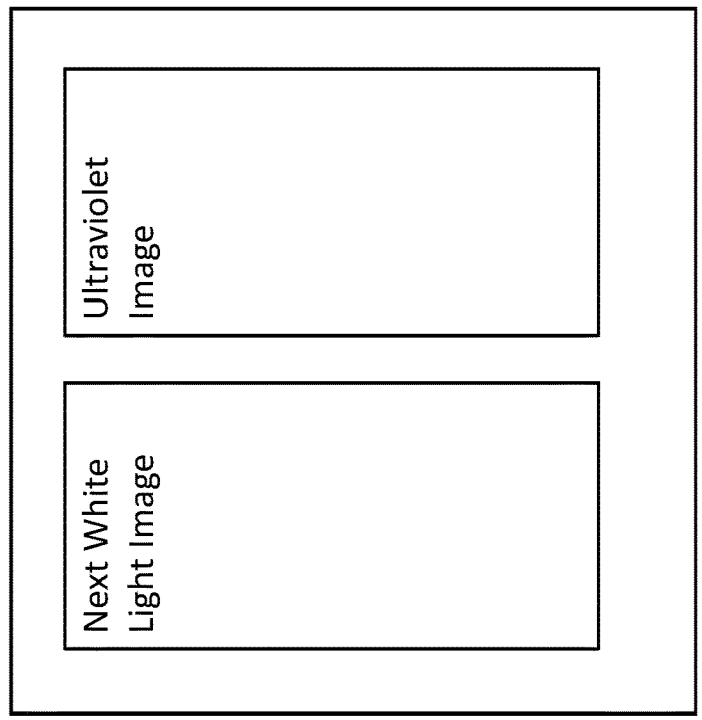
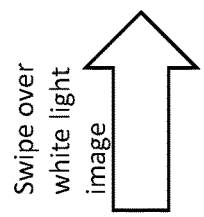
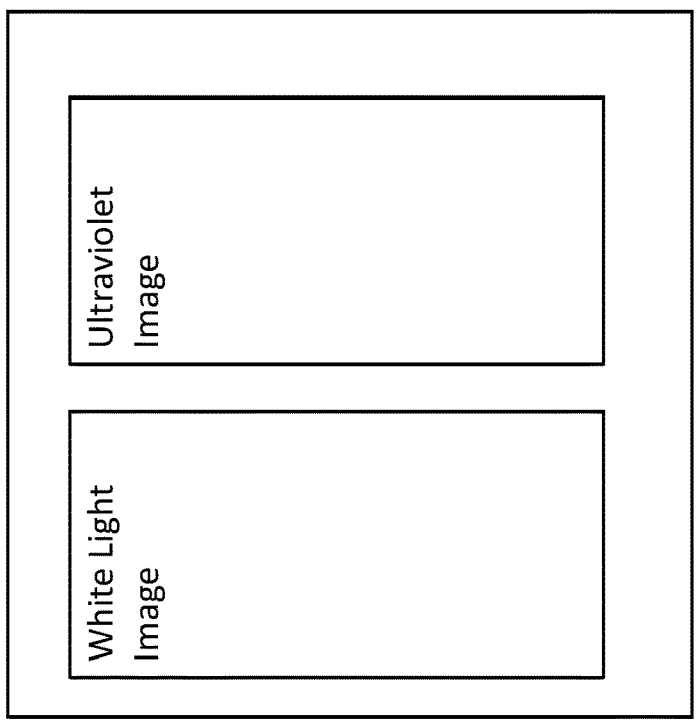
FIG. 7c

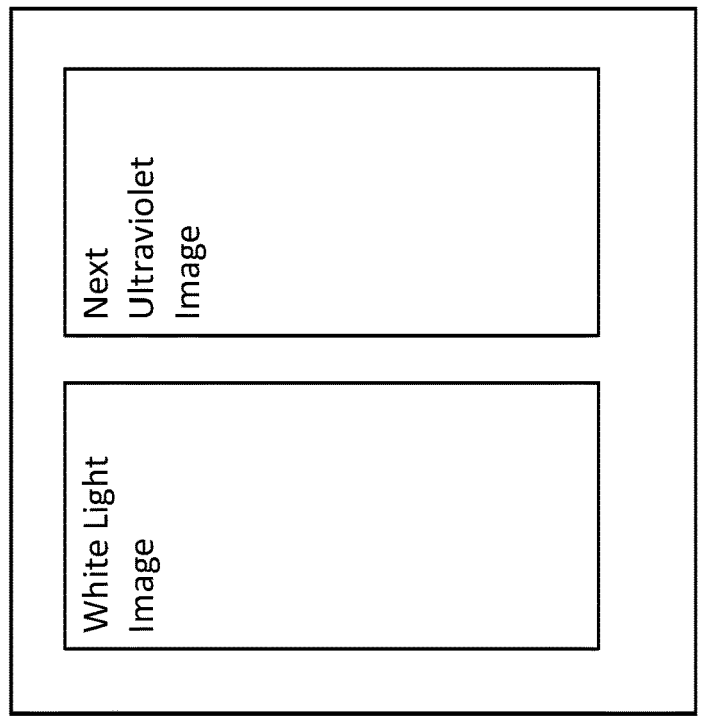
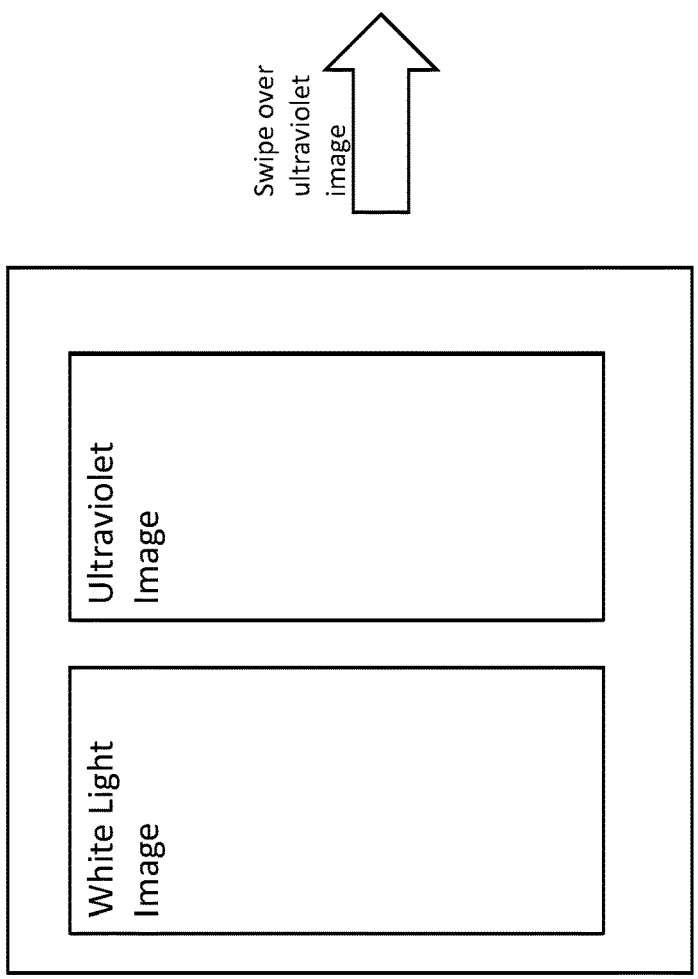
FIG. 7d

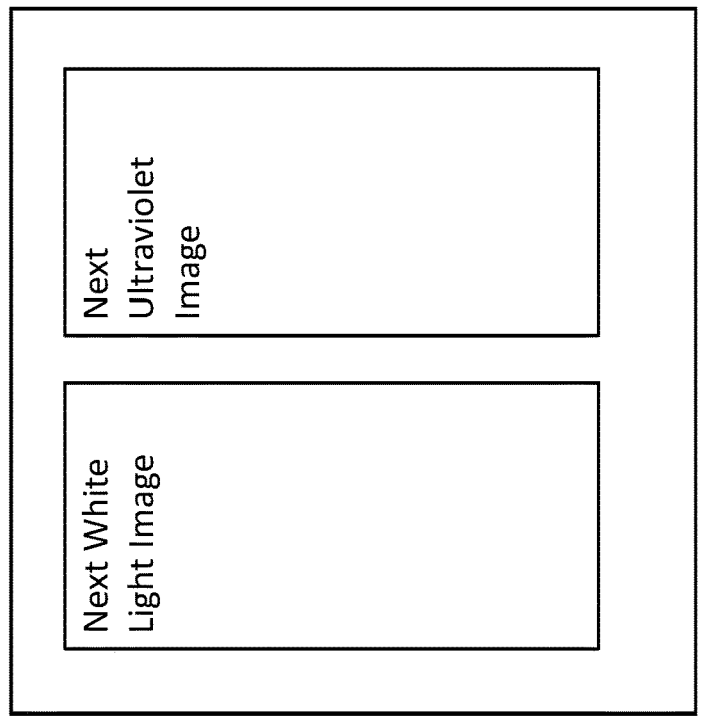
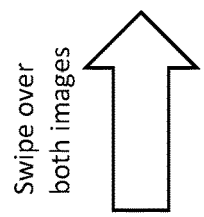
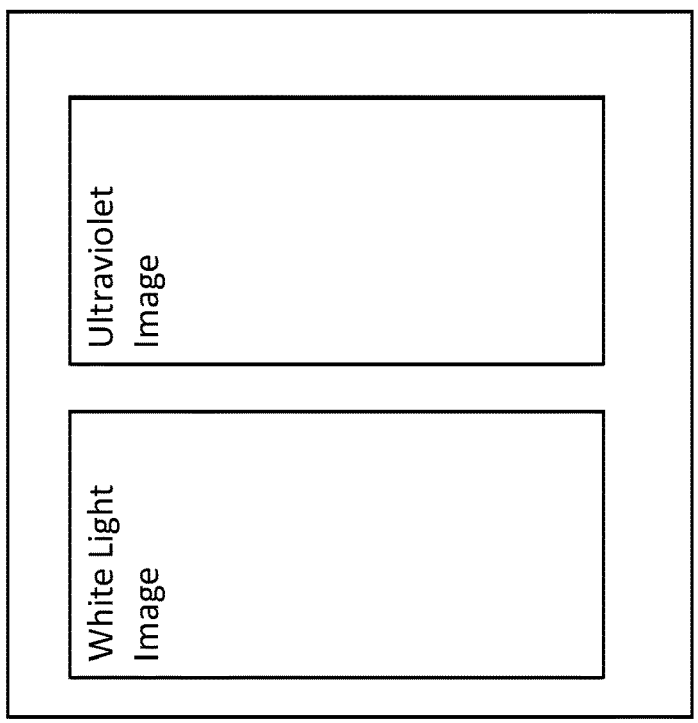
FIG. 7e

CONTEXT-AWARE USER INTERFACE FOR INTEGRATED OPERATING ROOM

FIELD OF THE INVENTION

The invention generally relates to interconnected medical devices and information systems that support surgical systems and surgical operations. The invention includes a control and/or control system that translates the user input into an appropriate control command to control various devices within the system.

BACKGROUND OF THE INVENTION

Modern Integrated Operating Rooms ("IOR") consist of interconnected medical devices and information systems. The typical IOR is a cluttered environment that is constituted of a myriad of medical devices, surgical instruments, monitors, touch screens, input devices (e.g. footswitches, computer keyboards and mouse, camera head buttons, etc.), communication systems, and so on. One reason for such clutter is that a multitude of equivalent input/output devices are needed by the surgical team to manage the flow of information and to control the different devices in the IOR. For example, multiple LCD displays are typically needed in the surgical field to view patient information (e.g., X-Rays, CT scans, MRI scans, vital signs, etc.), to display the surgical image and to control the IOR (e.g., using an IOR touchscreen or by voice and/or gesture control). Furthermore, it is not uncommon for a surgeon to have to operate an array of several footswitches, each triggering individual functions on different devices in the IOR.

To control the IOR, workflow management systems are used. Existing workflow management systems include U.S. Pat. No. 8,355,928 to Spahn; U.S. Patent Publication No. 2009/0125840 to Squilla et al.; U.S. Patent Publication No. 2010/0022849 to Franz et al.; U.S. Patent Publication No. 2008/0114214 to Messerges; U.S. Patent Publication No. 2008/0114212 to Messerges; Florent Lalys et al., Automatic knowledge-based recognition of low-level tasks in ophthalmological procedures, International Journal of Computer Assisted Radiology and Surgery, 2013, 8 (1), pp. 39-49; Houliston B R et al. (2011) TADAA: towards automated detection of anesthetic activity. Methods Inf Med 50(5): 464-471; N. Padoy et al., Statistical Modeling and Recognition of Surgical Workflow Medical/Image Analysis (2010), Volume 16, Issue 3, April 2012 (published online December 2010), pp. 632-641.

Other existing prior art includes: U.S. Pat. No. 8,411,034, "Sterile Networked Interface for Medical Systems" to Boillot et al.; U.S. Patent Publication No. 2009/0021475, "Method for displaying and/or processing image data of medical origin using gesture recognition" to Steinle et al.; U.S. Patent Publication No. 2012/0229383, "Gesture support for controlling and/or operating a medical device" to Hamilton et al.; U.S. Patent Publication No. 2013/0204428, "Method and device for controlling apparatus" to Steinle et al.; WO2011060187, "A master finger tracking device and method of use in a minimally invasive surgical system" Toltkowitz et al.; WO2011060185, "Method and system for hand presence detection in a minimally invasive surgical system" to Itkowitz et al.; WO2012044334, "Method and apparatus for hand gesture control in a minimally invasive surgical system" to Itkowitz et al.; WO2012129669, "Gesture operated control for medical information systems" to Tremain et al.; U.S. Patent Publication No. 2013/0225999, "Gesture commands user interface for ultrasound imaging systems" to Banjanin et al.; U.S. Patent Publication No. 2008/0253519, "Automatic Control of a Medical Device" to Bonfiglio et al.; WO2013038293, "Gesture-based user-interface with user-feedback" to Geurts et. al.; U.S. Patent Publication No. 2008/0114226, "Systems and methods for user interface and identification in a medical device" to Music et al.; U.S. Pat. No. 7,274,290, "Hygienic input device for medical information systems" to Morita et. al.; U.S. Patent Publication No. 2008/0104547, "Gesture-based communications" to Morita et al.; U.S. Patent Publication No. 2007/0118400, "Method and system for gesture recognition to drive healthcare applications" to Morita et. al.; and U.S. Patent Publication No. 2013/0179162, "Touch free operation of devices by use of depth sensors" to Merschon et al.

However, these existing systems suffer from various disadvantages. One disadvantage of existing systems is that existing systems have multiple devices that each have discrete functionality, such that clutter remains within the operating room.

Another disadvantage of existing systems is that the devices are not integrated with one another, as existing systems do not have a central device that is able to control the workflow of the medical procedure and that is able to use the workflow of the medical procedure to control data displayed on display monitors and interfaces.

Another disadvantage of existing systems involves having pre-programmed devices located within the operating room having limited usage within an operating room, as the pre-programmed devices do not have any means for interacting with other devices within the operating room.

Thus, there exists a need to provide a method and system that is able to overcome the disadvantages in existing systems to optimize and improve the workflow of a medical procedure and to reduce clutter in an operating room.

SUMMARY OF THE INVENTION

To improve upon the prior art, it is an object of the present invention to provide a workflow support system that is able to automatically detect and identify individual surgical phases and/or tasks, and to synthesize relevant information to one or more displays to optimize and improve the workflow of a medical procedure. Such an invention is driven by the workflow of the medical procedure and is augmented by context-awareness in the medical procedure.

Another object of the invention is to provide a system that is able to automatically navigate the workflow in an operating room to optimize the various settings that are required for each phase or task in a medical procedure. Such a system is intelligent and dynamic and allows for a context-driven procedure, where a user input is understood based upon the context and the workflow of the medical procedure, and is interpreted according to the particular stage of the medical procedure.

These and other objects of the invention are achieved by providing a system for managing workflow of a medical procedure, the system comprising: a control including a control processor, the control able to manipulate at least one medical device in the system via at least one control command, the control processor tracking the workflow of the medical procedure, whereby the workflow of the medical procedure occurs in particular stages; at least one detector, the at least one detector able to detect a user input during the medical procedure, the at least one detector being in communication with the control processor; wherein during a particular stage of the medical procedure, the at least one detector receives a user input and transmits a data signal to the control processor, wherein the control processor interprets the data signal from the user input according to the particular stage of the medical procedure to determine at least one control command to send to the at least one medical device at least in part based upon the particular stage of the medical procedure, wherein the control processor sends the at least one control command to the at least one medical device to manipulate the at least one medical device.

In certain embodiments, the at least one detector is a sensor. In certain embodiments, the at least one detector is a multi-modal sensor.

In certain embodiments, during a first stage of the medical procedure, the user input corresponds to a first command determined by the control, and during a second stage of the medical procedure, the user input corresponds to an second command determined by the control, the first command and the second command being based at least in part upon the particular stage of the medical procedure. In certain embodiments, the first command and the second command are different. In certain embodiments, the first command and the second command are the same.

In certain embodiments, the system further comprises a database storing clinical information; at least one display displaying a user interface; and software executing on said processor for displaying a subset of the clinical information on said at least one display monitor via the interface.

In certain embodiments, a different subset of the clinical information is displayed on the at least one display for each stage of the medical procedure, the medical procedure being a multi-stage medical procedure.

In certain embodiments, the control is aware of the subset of the clinical information displayed on the interface of said at least one display monitor and interprets the at least one control command at least in part based upon the user input, the clinical information displayed on the interface and the particular stage of the medical procedure.

In certain embodiments, the control correlates the user input with a particular stage of the medical procedure.

In certain embodiments, the at least one medical instrument manipulated by the control is the at least one display. In certain embodiments, the at least one medical instrument involves multiple display and/or display monitors.

In certain embodiments, the at least one medical instrument involves visual imaging tools (e.g. endoscopes, cameras, digital x-ray, ultrasound, computer tomography, magnetic resonance imaging). In certain embodiments, the at least one medical instrument is a laryngoscope, endoscope, scalpel, intubation tube, stent, and/or other such medical devices that a user (such as a surgeon or nurse) may use during a medical procedure. In certain embodiments, that at least one medical device is a tool for cutting, grasping, extracting, irrigating, etc. In certain embodiments, the at least one medical device includes other operating room equipment.

In certain embodiments, the workflow of the medical procedure is controlled at least in part by the control. In certain embodiments, subsequent steps of the medical procedure are controlled at least in part by the control. In certain embodiments, subsequent steps of the medical procedure are controlled totally by the control.

In certain embodiments, the at least one medical device includes at least one medical device control, wherein the at least one medical device control performs a different task during different stages of the multi-stage medical procedure.

In certain embodiments, the at least one medical device control is able to be reprogrammed to perform a different task during different stages of the multi-stage medical procedure.

In certain embodiments, the system further comprises an image recognition module able to detect a stage of the medical procedure to at least partially determine the subset of clinical information that is displayed on the at least one display monitor. In certain embodiments, the image recognition module is located within the control and/or is part of the control.

In certain embodiments, the user input is speech recognition and/or gesture control.

In certain embodiments, the system further comprises a hazard mitigation module. In certain embodiments, the hazard mitigation module is software that is executed by the software in the control or in a processor. In certain embodiments, the hazard mitigation module filters out user input that are not appropriate in the particular stage of the medical procedure.

In certain embodiments, during the medical procedure, the control updates the progress of the medical procedure by providing updates through the at least one display monitor.

In certain embodiments, the clinical information is divided into subsets according to the authorization level or permission level of an intended recipient of the clinical information.

In certain embodiments, the system further comprises at least two display monitors, wherein at least one display monitor displays a subset of information that is relevant for a first intended recipient, and wherein at least one display monitor displays a subset of information that is relevant for a second intended recipient.

In certain embodiments, each of the displays has at least one detector (e.g., motion sensor, proximity sensor, microphone(s), camera, etc.) to detect user intent to interact with the content of the display.

In certain embodiments, the at least one detector is a sensor. In certain embodiments, the at least one detector is a device that is able to receive the input from the user. In certain embodiments, the at least one detector is a microphone or device able to interpret speech commands. In certain embodiments, the at least one detector is a device able to interpret gesture commands.

Other objects of the invention are achieved by providing a method for managing workflow of a medical procedure, the method comprising: providing a control including a control processor, the control able to manipulate at least one medical device in the system via at least one control command, the control tracking the workflow of the medical procedure, whereby the workflow of the medical procedure occurs in particular stages; providing at least one detector, the at least one detector able to detect a user input during the medical procedure, the at least one detector being in communication with the control processor; receiving a user input during a particular stage of the medical procedure; correlating the user input with a particular stage of the medical procedure; determining the at least one control command to send to the at least one medical device based at least in part upon the correlation of the user input and the particular stage of the medical procedure; and sending the at least one control command to the at least one medical device to manipulate the at least one medical device.

In certain embodiments, during a first stage of the medical procedure, the user input corresponds to a first command determined by the control, and during a second stage of the medical procedure, the user input corresponds to a second command determined by the control, the first command and the second command being based at least in part by the particular stage of the medical procedure.

In certain embodiments, the method further comprises providing a database storing clinical information; providing at least one display monitor having an interface; and providing software executing on said processor for displaying a subset of the clinical information on said at least one display monitor via the interface.

In certain embodiments, a different subset of the clinical information is displayed on the at least one display monitor for each stage of a multi-stage medical procedure.

In certain embodiments, the control is aware of the subset of the clinical information displayed on said at least one display monitor via the interface and interprets the at least one control command based at least in part upon the user input, the clinical information displayed on said at least one display via the interface and based at least in part on the particular stage of the medical procedure.

In certain embodiments, the clinical information displayed on the at least one display monitor is for a multi-stage medical procedure.

In certain embodiments, the at least one medical device is an input device that can be dynamically re-programmed. In certain embodiments, at least two display monitors are provided.

In certain embodiments, the user input is speech recognition and/or gesture control. In certain embodiments, the user input is received by a microphone. In certain embodiments, the user input is received by any device that can interpret a speech command or a gesture command.

Other objects of the invention are achieved by providing a system for managing workflow of a medical procedure, the system comprising: a control including a control processor, the control able to manipulate at least one medical device in the system via at least one control command, the control processor tracking the workflow of the medical procedure, whereby the workflow of the medical procedure occurs in particular stages; at least one detector, the at least one detector able to detect a user input during the medical procedure, the at least one detector being in communication with the control processor; wherein the at least one detector receives a user input and transmits a data signal to the control processor, wherein the control processor interprets the data signal from the user input to determine at least one control command to send to the at least one medical device.

In certain embodiments, the detector is a multi-modal sensor.

In certain embodiments, the multi-modal sensor is able to detect a second user input, the second user input being of a different format than the user input.

In certain embodiments, the controller is configured to send the at least one control command to at least two medical devices, the at least one control command being able to control the at least two medical devices.

In certain embodiments, the system further comprises a hazard mitigation module, the hazard mitigation module being able to mitigate errors in interpreting the user input.

Other objects of the invention are achieved by providing a detector, the detector configured to detect a user input during the medical procedure, the detector configured to interpret an input from a user, and use the input to control at least one medical device in an operating room.

In certain embodiments, the detector is in communication with a control processor. In certain embodiments, the detector is configured to transmit a data signal to the control processor.

In certain embodiments, the detector is associated to a specific device according to an association database. In certain embodiments, the association database includes information about the detector, about the type of input (e.g., set of gestures or voice commands) that the detector can accept, about the target device for each input, and the control command corresponding to the input. In certain embodiments, the association database includes the above information for a multitude of detectors. In certain embodiments, the control processor queries the association database to determine at least one control command to send to the at least one medical device.

In certain embodiments, the control processor interprets the data signal from the user input to determine at least one control command to send to the at least one medical device.

In certain embodiments, the input from the user is during a medical procedure. In certain embodiments, the detector is manipulated by a control, the control configured to track the workflow of the medical procedure, whereby the workflow of the medical procedure occurs in particular stages.

In certain embodiments, the detector is manipulated via at least one control command from the control processor.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

BRIEF DESCRIPTION OF THE DRAWINGS

FIGS. 7a-7e show various embodiments of the display having Picture-in-Picture (PiP) and Picture-and-Picture (PaP, or side-by-side) functionality.

DETAILED DESCRIPTION OF THE INVENTION

Figure 1:
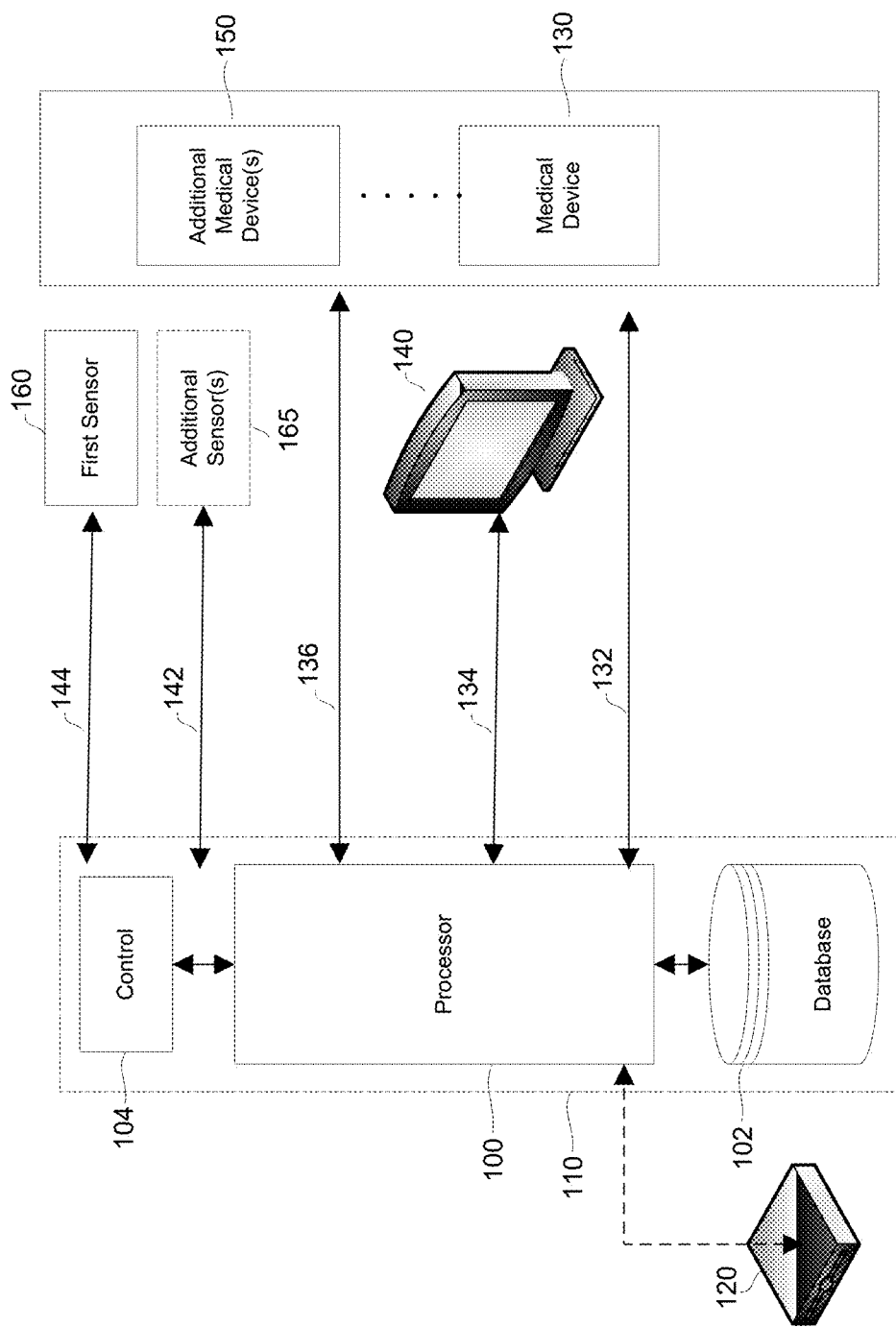
FIG. 1 is a schematic view of a surgical workflow support system of an embodiment of the present invention.

In the following description, numerous details are set forth for purpose of explanation. However, one of ordinary skill in the art will realize that the invention may be practiced without the use of these specific details. For instance, the techniques described below are described in a specified order, but other embodiments may change the order of the operations while still embodying the current invention.

The present invention relates to Integrated Operating Room ("IOR") or ("OR") solutions and in particular to the KS OR1 Fusion system developed by the Karl Storz®. OR1 Fusion provides a control station allowing control of several components of an Integrated OR, including Capture, Routing, SCB, Checklist, Entertainment, Telephone, Lights, etc.

In prior art systems, control of such devices is only possible by means of a dedicated touch screen and/or keyboard/mouse combination for each of the devices. Other auxiliary input devices (e.g., camera head buttons, foot pedals) can be assigned to trigger a limited number of pre-determined actions (e.g., take a still, record video, etc.). Such auxiliary input devices are pre-programmed, and because it is inconvenient for a user to change such programming during a surgery, their usage is normally limited. Furthermore, other devices like surgical screens are normally within reach of the surgeon, but since they are passive devices, they do not offer any means for interacting with their content.

The present invention consists of an Integrated OR with one or more displays (display monitors, LCD screens or other types of devices that display information). The invention also includes a control or control station that is aware of the current state of the IOR and workflow ("context awareness"), and in particular of the content that is displayed on each of the displays. The control is able to control the content displayed on these displays based upon the workflow of the surgical procedure. The user input is interpreted in accordance with the workflow to control the displays as well as other devices within the IOR.

Incorporated by reference into this application is U.S. patent application Ser. No. 13/949,724 entitled "Multi-Dimensional Surgical Safety Countermeasure System" filed on Jul. 24, 2013. The content of U.S. patent application Ser. No. 13/949,724 is incorporated into this application in its entirety.

Incorporated by reference into this application is U.S. patent application Ser. No. 14/279,015 entitled "Surgical Workflow Support System" filed on May 15, 2014. The content of U.S. patent application Ser. No. 14/279,015 is incorporated into this application in its entirety.

Also incorporated by reference into this application is U.S. patent application Ser. No. 11/527,142 entitled "System And Method For Hazard Mitigation In Voice-Driven Control Applications" filed on Sep. 26, 2006. The content of U.S. patent application Ser. No. 11/527,142 is incorporated into this application in its entirety.

Objects of the present invention are achieved by various additional capabilities outlined below:

I. Interface Driven by Surgical Workflow and Augmented by Context-Awareness

In certain embodiments of the present invention, the system is able to understand the workflow of a medical procedure, such as a surgery, and thus is able to control the information shown on one or more displays during a particular phase of the surgical workflow.

In certain embodiments, the system has one or more display monitors. Each of the display monitors has one or more associated detector device (e.g., motion sensor, proximity sensor, microphone(s), camera, etc.) to detect user intent to interact with the content provided on the display device. In certain embodiments, the control in the system interprets the user intent based on its current context (e.g., current workflow step, screen content, etc.) and translates it into an appropriate command to the display monitor and/or to a medical device in the operating room.

The present invention provides a context and workflow aware IOR system enabling users to interact with passive devices in the operating room by interpreting user input—according to the current context and/or workflow phase—received at one or more sensors. In certain embodiments, the present invention provides use of multiple sensors, sensor types and input modalities that support an intelligent user interface that is intuitive and simple to use.

FIG. 1 shows an exemplary system for managing workflow of a medical procedure in an operating room. The system includes at least one processor 100. The processor 100 may be any device, system or part thereof that controls at least one operation and/or executes software applications or machine-readable instructions. The processor 100 may be implemented in hardware, firmware or software, or some combination of at least two of the same.

The processor may also comprise memory storing machine-readable instructions executable for performing tasks. A processor acts upon information by manipulating, analyzing, modifying, converting or transmitting information for use by an executable procedure or an information device, and/or by routing the information to an output device. It should be noted that the functionality associated with any particular processor may be centralized or distributed, whether locally or remotely. In some embodiments, the processor 100 is included in a server 110. In other embodiments, the processor 100 is included in a computer 110. In other embodiments, the server 110 is a computer.

In certain embodiments, the processor is able to process clinical information such as patient data or medical data. In certain embodiments, the processor is located within a computer or a server. In certain embodiments, the processor executes instructions that are stored on a memory or a computer medium.

As defined herein "clinical information" is information that is related to a clinical or medical procedure. Clinical information includes medical data and patient data. Such medical data may include but is not limited to a patient's heart rate, blood pressure, sugar levels, and other such data that is important to monitor during a medical procedure. Clinical information may also include diagnostic medical data such as X-Rays, CT scans. MRI scans, lab results, stills and videos from past procedures, etc.

In certain embodiments, clinical information also comprises information that is exchanged between connected IORs. For example, in a living-donor kidney transplant surgery, the system monitors the progress of the surgery on the donor and provides relevant information to the surgical team of the recipient so that the two surgeries can proceed in synchronous steps, and so that the recipient is ready to receive the organ when the organ has been extracted from the donor. The system may also monitor both surgeries simultaneously, so that if for example the surgical steps on the recipient incur some delaying complications, then the system may instruct the surgical team on the donor side to slow down the procedure.

In certain embodiments, clinical information is divided in subsets according to the role of the intended recipient. For example, one or more display monitors in the surgical field may display a subset of information that is relevant for the surgeon, while a display monitor at the nurse's station or near the instrument cart may display a subset of information that is relevant for a nurse.

As defined herein, a "subset" of clinical information is a set of clinical information that is less than the total set of clinical information stored on a computer or server. For example, a subset of clinical information may include a set of information related to a patient's blood pressure and pulse, which is a smaller set than all the clinical information of the patient that is maintained by a computer and/or server (e.g., the computer may maintain additional clinical information such as X-Rays, MRI scans, a patient's sugar levels and other such clinical information, while only displaying "subsets" of the information at a time).

Various subsets of data can be displayed based upon the particular stages of a medical procedure. In this manner, only a subset of clinical information that is relevant to a step in the medical procedure is displayed and a different subset of clinical information can be displayed during a different step of the medical procedure. In certain embodiments, the same subset of information can be displayed in different steps if necessary for the medical procedure.

Referring to FIG. 1, the processor may also comprise a control 104. As shown in FIG. 1, the processor and control are linked to a first sensor 160 and to additional sensor(s) 165. The first sensor 160 and the additional sensor(s) are detectors that can detect a user input and can detect user intention. The user input could be a voice command, a gesture, and or another type of command that is detected by a detector, such as a sensor, and then transmitted to the control and processor for processing the input.

In the system, the control 104 is aware of the current state of the operating room and the workflow of the medical procedure. In particular, in certain embodiments, the control is aware of the content that is displayed on display monitor 140, which is shown in FIG. 1 as connected to the processor.

In certain embodiments, the at least one display 140 is a display monitor is able to display the clinical information or a subset of clinical information. In certain embodiments, the at least one display monitor includes a graphical user interface ("GUI") and at least one dashboard, the at least one dashboard able to display clinical information on the display monitor.

A "dashboard" as defined herein is one or more window panes for providing information. Window panes can be provided for a specific view for one or more clinical data items. For instance, these windows might show different information for a particular patient. One window pane might show a CT scan of the patient, the other window pane might show a lab report, and the third window might show a graph of oxygen saturation.

In certain embodiments, the control interprets the user input received by first sensor 160 and additional sensor(s) 165 according to the data displayed on display 140 and transmits a command to the display 140 or to a medical device 130 or an additional medical device. In this way, the control 104 is able to control the workflow of the medical procedure, which drives the information able to be displayed on the at least one display monitor. The control 104 interprets the user intent based on its current context (e.g., current workflow step, screen content, etc.) and translates it into an appropriate command, which affects the content shown on the display 140.

In certain embodiments, the control applies one or more rules determined according to the data displayed on display 140 to interpret the user input. In certain embodiments, such rules are stored on one or more database(s) 102.

Referring to FIG. 1, the system further includes one or more database(s) 102. The database(s) 102 may be local to the processor 100 and/or server or computer 110, or distributed and remote to the processor 100 and/or server or computer 110. For example, database 102 may be included on any hard disk or hard drive, an external storage device and/or portable media, such as a compact disc ("CD") or digital versatile disc ("DVD") accessible by a portable media device 120. The database 102 includes any number of directories and subdirectories including a plurality of electronic files accessible by the system. The files may be any electronic files of a particular type or many different types.

In certain embodiments of the invention, a user input or intention is dynamically paired with one or more of the devices controlled by the control. For example, the system may include using proximity sensors, or special gestures to enable interaction with specific devices, as well as camera input (user identification, eye gaze detection), and special markers to identify authorized users. The system then correlates input received by these devices to control the display monitors in the system as well as other devices in the operating room.

In certain embodiments, the control 104 provides configurable mappings between gestures/control devices and the corresponding actions to trigger. Such mappings can be stored in user profiles, or a set of pre-built profiles can be provided. In certain embodiments, database 102 can store user profiles and store mappings between gestures/control devices and the corresponding actions to trigger.

In this manner, a control 104 can be customized based upon a specific medical procedure or medical team. For example, a heart transplant operation will have a different set of actions to trigger than an endoscopic surgery to remove a tumor. Additionally, different surgeons can customize the control based on their preferences and the control 104 is intelligent, such that it is able to adapt to a surgeon's preference based upon patterns through multiple surgeries by that surgeon.

The preferences, rules and mappings can be stored in one or more databases in the operating room or located external to the operating room.

The system further includes a communication link 132 to link the processor 100 to a medical device 130 via software executing on the processor, on the medical device, or on both. For example, a user may use the medical device 130 (e.g., a scalpel) and the medical device 130 may be connected with the processor 100. In certain embodiments, the communication link 132 connects the medical device 130 to the processor 100 by wireless technology (such as WiFi, BLUETOOTH, ZigBee, optical or ultrasonic communication). In other embodiments, the medical device 130 is connected to the processor 100 by a wire or cable. In certain embodiments, the medical device 130 includes a sensor, an RFID tag, or a type of active or passive identifier that interacts with the computer and with the control 104 and processor 100.

In certain embodiments of the system, when the sensor 160 receives a user input, information is sent to the control 104 that the sensor is actuated. The control 104 and processor 100 then, send a command to the medical device 130 and/or display 140 based upon the context and/or or current state of the operating room and workflow.

For example, when a DICOM viewer is displayed on a display monitor 140, a swipe gesture in front of that display monitor 140 switches to the next image. In this manner, the swipe gesture is interpreted by the detector 160, which sends data to the control 104. The control 104 then sends a control command to the DICOM viewer to show the next image on display monitor 140.

If the same display monitor 140 is showing the surgical image, the same swipe gesture may switch the input source or start recording. And if the monitor is showing playback of a previously recorded video, the swipe gesture may trigger a fast forward action. In this manner, the context of the particular stage of the medical procedure is correlated with the user input, such that the context of the medical procedure in combination with the user input is used to send a particular command to the display to perform a certain function or to display a certain subset of data.

In certain embodiments of the invention, multiple video signals are combined on a single display monitor, in a Picture-in-Picture (PiP), Picture-and-Picture (PaP, or side-by-side), quad-view, or other arrangement. In certain embodiments, the detector 160 sends information about the user input to the control 104 that is augmented by a set of coordinates identifying the area affected by the user input. In this manner, the control 104 can associate the user input to a particular device according to the area. For example, control 104 may send to display monitor 140 the surgical image as full screen video, and an image from the DICOM Viewer in the PiP slot. In this example, a swipe gesture over the area showing the surgical image may trigger a switch of input source (FIG. 7A), while a swipe gesture over the smaller area occupied by the PiP image causes the DICOM Viewer to show the next image (FIG. 7B). In certain embodiments, if the area affected by the user input spans over multiple view regions, the control 104 may apply the user input to each of the corresponding devices. For example, a set of stereo images taken with different light exposures (e.g., white-light and ultraviolet) can be shown on display 140 in a PaP arrangement, white-light on the left and ultraviolet on the right side. In such example, a swipe gesture over the left side of the monitor will cause the control 104 to display the next white-light image (FIG. 7C), a swipe gesture over the right side of the monitor will cause the control 104 to display the next ultraviolet image (FIG. 7D), and a swipe gesture encompassing both the left and the right side will advance both images (FIG. 7E).

In certain embodiments of the invention, the ability to turn non-interactive devices into devices capable of receiving user input is not limited to display monitors or video displays. Other devices, even those that normally have no or little user interface, can be enabled to accept user input, provided that the operating room is augmented with the appropriate sensors. Such devices can include passive devices that are typically located in an operating room such as a laryngoscope, endoscope, scalpel, intubation tube, stent, and/or other such medical devices that a user (such as a surgeon or nurse) may use during a medical procedure.

In certain embodiments of the invention, for example, a thumbs-up gesture can be interpreted to raise the background music volume. The same thumbs-up gesture towards a lightsource device would instead raise the light intensity. In the example, input from the sensor in front of the lightsource device would cause control 104 to raise the light intensity, while input from the sensor hanging in the center of the operating room or by a speaker system would cause control 104 to raise the background music volume.

In certain embodiments, the present invention allows for the type of user input to include different modalities, for example gestures combined with speech recognition, which can enable more complex actions or provide a higher confidence in the detected user intent. In this manner, sensor 160 detects a gesture and sensor 165 detects a voice command to enable more actions or provide a higher confidence in the detected user intent.

For example, a surgeon may give a thumbs-up gesture and say "raise the music." In this manner, there is higher confidence to raise the background music volume than to raise the light intensity of a light source. Additionally, a surgeon may swipe in front of a monitor and say "record," which would be an example of a more complex action, and would cause the system to switch to the next image and begin recording the medical procedure.

Also, user input in additional modalities can provide redundant confirmation to mitigate against unintended, possibly hazardous actions. Such integration of multiple input modalities (gestures, speech recognition, gaze tracking, etc.) supports intuitive and rich user commands. In such embodiments, multiple detector devices, such as sensors 160 and 165 are used to combine gestures and speech recognition, such that the control 104 can understand user intent, and to reduce error within the system when interpreting user input.

In other embodiments a single detector device is used to detect multiple input modalities, and is a multi-modal detector. In certain embodiments, single error in a multi-modal input system can be detected and mitigated.

In certain embodiments, since the control is aware of the surgical workflow, interaction with certain devices via gestures and/or speech recognition can be allowed only during appropriate phases of the workflow, and certain commands can be disabled based upon the stage of a workflow.

In certain embodiments, for example, during the setup phase of a laparoscopy procedure a thumbs-up gesture may increase the insufflator pressure, whereas in arthroscopy a thumbs-up might increase the iPod® volume. Similarly, during the actual procedure the surgeon's hands are busy and so interpretation of hand gestures are disabled. Accordingly, in certain embodiments, the control includes rules that disable certain functions depending upon the stage of the medical procedure.

Referring again to FIG. 1, the processor 100 is linked to a display 140 by a communication link 134. In certain embodiments, the communication link 134 connects display 140 to the processor 100 by wireless technology. In certain embodiments, the display 140 includes a sensor, an RFID tag, or a type of active or passive identifier that interacts with the computer. In other embodiments, the display 140 is connected to the processor 100 by a wire or cable.

In FIG. 1, processor 100 also may be linked to additional medical device(s) 150 via communication link 136. In certain embodiments, the communication link 136 may be wireless or via a hardwire. In certain embodiments, additional medical device(s) 150 may include as many medical devices 150 as necessary to perform the medical or surgical procedure.

In certain embodiments of the invention, the medical device may consist of medical devices such as a laryngoscope, endoscope, scalpel, intubation tube, stent, and/or other such medical devices that a user (such as a surgeon or nurse) may use during a medical procedure. In certain embodiments, the medical device includes input devices such as a keyboard, mouse, touch screen and/or a, footpedal.

Figure 2:
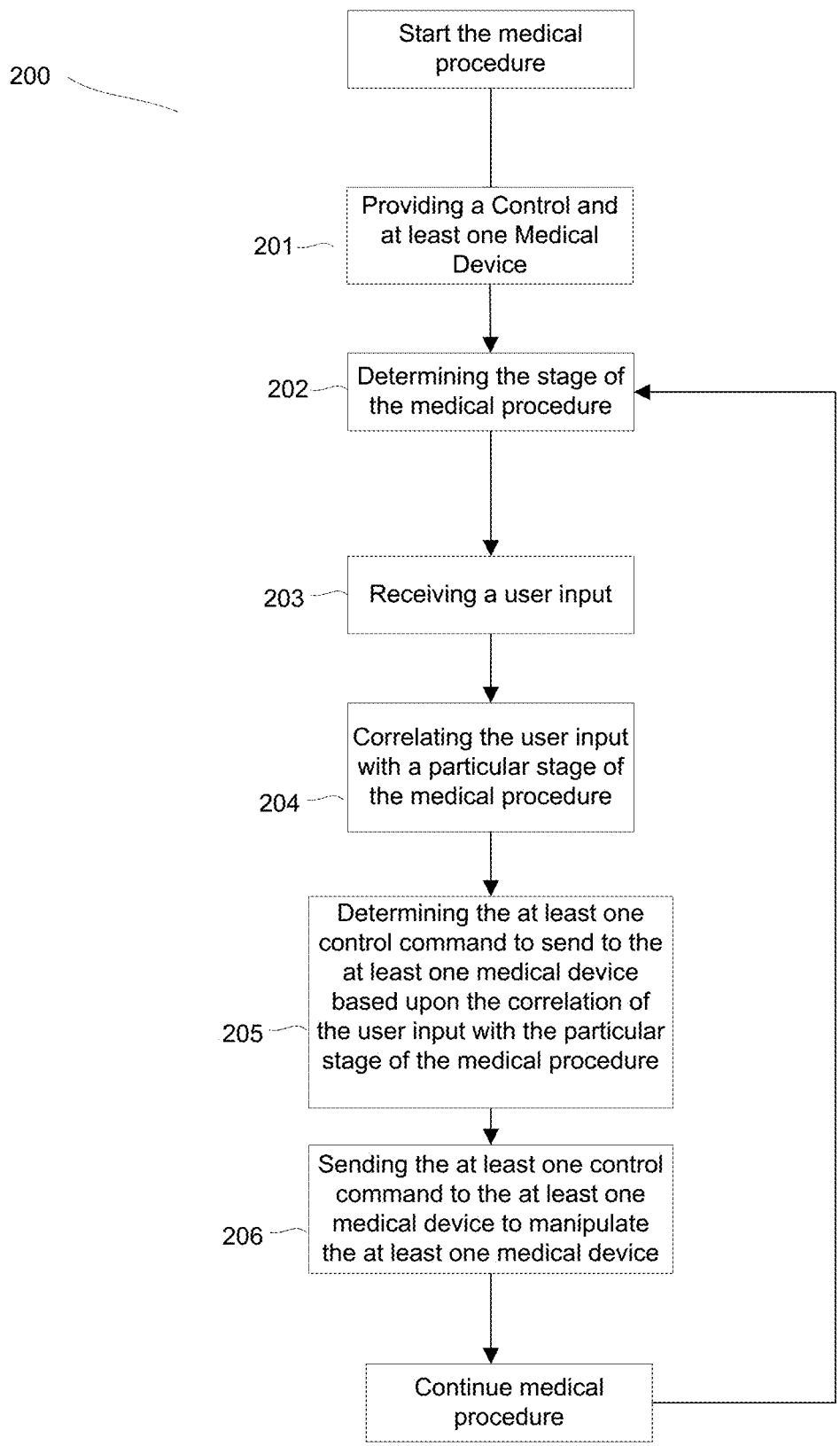
FIG. 2 is a flowchart of an embodiment of the present invention.

Referring to FIG. 2, a method 200 is provided for managing workflow of a medical procedure. Method 200 involves steps for providing a control and at least one medical device 201, determining the stage of a medical procedure 202, receiving a user input 203, correlating the user input with a particular stage of a medical procedure 204, determining the at least one control command to send to the at least one medical device 205, and sending the at least one control command to the at least one medical device to manipulate the at least one medical device 206.

In this manner, the control determines the control command depending on the particular stage of the medical procedure and the user input. This can occur multiple times in a medical procedure and different user commands have a different result depending on the particular stage of the medical procedure. In certain embodiments, the same user command may have different results depending on the particular stage of the medical procedure.

In certain embodiments, the correlation occurs based upon the data shown in one or more display monitors.

Figure 3:
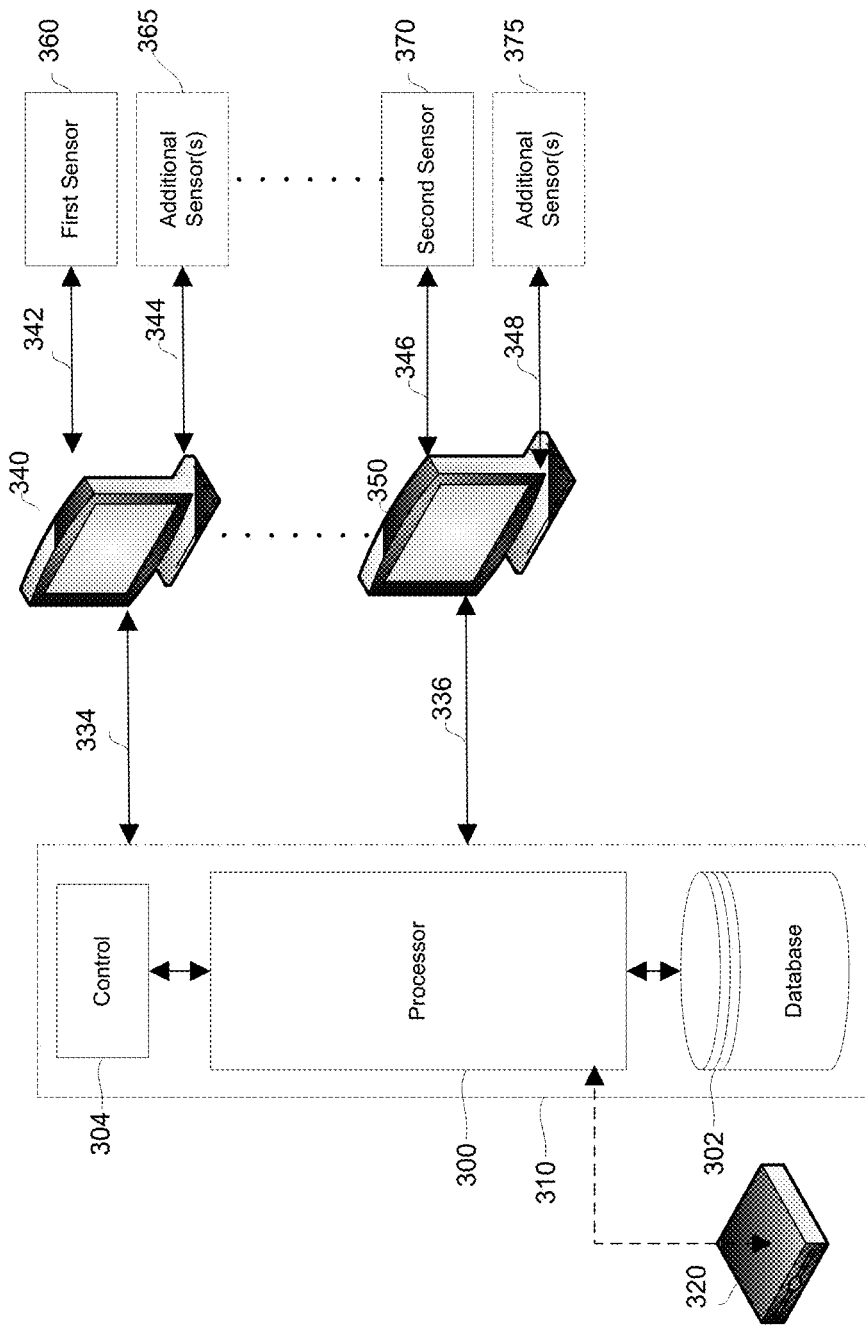
FIG. 3 is a schematic view of a surgical workflow support system of an embodiment of the present invention.

Referring to FIG. 3, another exemplary system for managing workflow of a medical procedure in an operating room is provided. The system includes at least one processor 300. In some embodiments, the processor 300 is included in a server 310. In other embodiments, the processor 300 is included in a computer 310. In other embodiments, the server 310 is a computer.

The processor also comprises a control 304, the control linked to a first display 340 via communication link 334. First display 340 is connected to first sensor 360 and to additional sensor(s) 365 via communication link 342 and 344 respectively. The first sensor 360 and the additional sensor(s) 365 are detectors that can detect a user input. The user input could be a voice command, a gesture, and or another type of command that can be understood by a sensor. In certain embodiments, the first sensor and additional sensor can work together to interpret user intent.

The processor 310 may also be linked to a second display (additional display) 350 via communication link 336. Second display 350 is connected to second sensor 370 and to additional sensor(s) 375 via communication links 346 and 348 respectively. The second sensor 370 and the additional sensor(s) 375 are detectors that can detect a user input. The user input could be a voice command, a gesture, and or another type of command that can be understood by a sensor. In certain embodiments, the second sensor and additional sensors can work together to interpret user intent.

The control 304 is aware of the current state of the operating room and the workflow of the medical procedure. In particular, the control is aware of the content that is displayed on the first display 340 and second display 350.

The control 304 interprets the user intent based on its current context (e.g., current workflow step, screen content, etc.) and translates it into an appropriate command. The command is sent to the appropriate display 340 and/or 350. Additionally, the system shown in FIG. 3 also includes the advantages recited with regards to other embodiments of the invention, specifically as shown and described in FIG. 1.

II. Hazard Mitigation

In certain embodiments of the invention, user intent is based on gestures and/or speech recognition, and there is the potential for misinterpretation errors in the system. Accordingly, another object of the invention involves mitigation of possible hazards in the system using various hazard mitigation measures.

The present invention provides implementation of hazard mitigation measures to prevent unintended activation of critical commands. In certain embodiments, the present invention provides appropriate hazard mitigation measures that can be triggered by an unintended or misinterpreted command or gesture.

Figure 4:
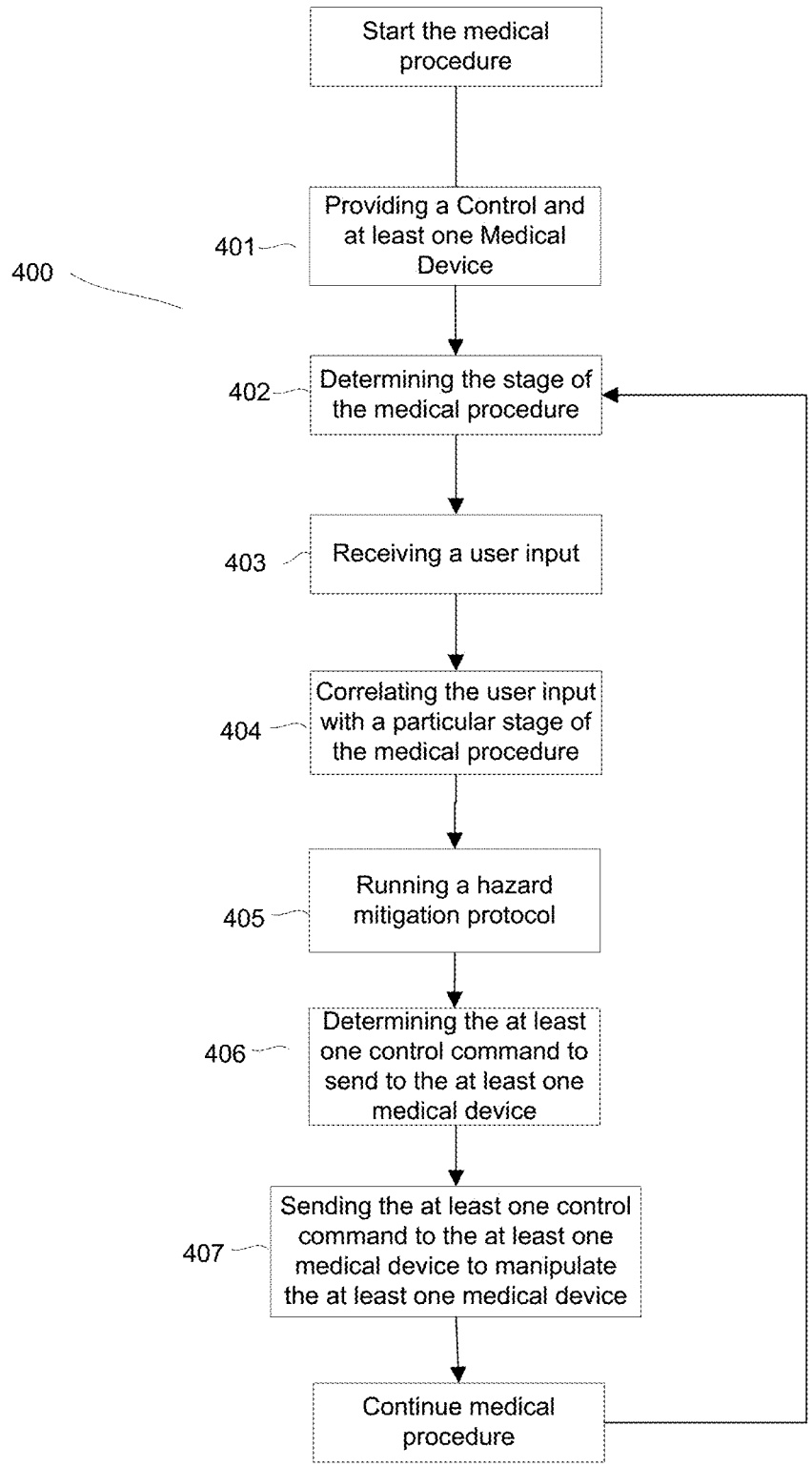
FIG. 4 is a flowchart of an embodiment of the present invention.

In FIG. 4, a hazard mitigation protocol 400 is provided. Method 400 involves steps for providing a control and at least one medical device 401, determining the stage of a medical procedure 402, receiving a user input 403, correlating the user input with a particular stage of a medical procedure 404, running a hazard mitigation protocol 405, determining the at least one control command to send to the at least one medical device 406 if the hazard mitigation protocol is satisfied, and sending the at least one control command to the at least one medical device to manipulate the at least one medical device 407.

In this manner, a hazard mitigation protocol is used in the system. Such hazard mitigation protocols are provided, for example, in U.S. patent application Ser. No. 11/527,142 entitled "System And Method For Hazard Mitigation In Voice-Driven Control Applications" filed on Sep. 26, 2006.

The content of U.S. patent application Ser. No. 11/527,142 is incorporated into this application in its entirety.

Other hazard mitigation measures involve various functionality and commands being disabled, such that certain functionality is only available based at least in part on certain stages of the medical procedure.

By disabling various functions during certain stages of the medical procedure by the control (104, 304), safety of the procedure is increased, as there is no risk of having various functions performed in the medical operating room when the function is disabled.

In certain embodiments of the present invention, devices and commands are classified into different hazard categories, and potentially hazardous commands are only allowed when there is high confidence on the input (based on proximity, modality, composition of modalities, etc.). The use, or requirement, of multiple input modalities can be leveraged for increased safety.

In certain embodiments, the potentially hazardous commands are stored in a database, such that when the potentially hazardous commands are detected by the detector, the potentially hazardous commands are compared with rules, such that additional input is required in order to execute the potentially hazardous commands.

In certain embodiments, the control (104, 304) is able to process such potentially hazardous commands to determine whether or not a hazardous command has been given and whether the system is to execute a function associated with the command.

Additionally, hazard mitigation can be implemented effectively in conjunction with workflow assistance. The knowledge of the current state in the medical procedure can be utilized to filter out certain commands that are not appropriate in the current stage. For example, in a preoperative stage, a swipe gesture towards the surgical monitor can be interpreted as an intention to view the next image (e.g., in an X-ray set). However, once the procedure is in the operative stage (more specifically, in a potentially hazardous surgical step like, e.g., when the surgical workflow system is expecting the next step to be an incision), the system may prevent the same swipe gesture from switching away from the live surgical feed.

In certain embodiments, the hazard mitigation feature prevents spurious gestures (e.g., from other people in the room, or misinterpreted gestures) from triggering such actions.

In certain embodiments, the use of confirmation feedback (audible confirmation, or video overlay) is another example of hazard mitigation.

Hazard mitigation is another feature of a multi-modal sensor, since each individual "recognition" technology (gesture, voice, and image) can have interpretation errors, but since these errors are likely uncorrelated across technologies, any single error in a multi-modal input system can be detected and mitigated.

III. Cross-Talk and User Feedback

In certain embodiments, possible collisions or cross-talk between the different sensors in the room are automatically detected and a proper alarm can be triggered, and/or (a subset of) the affected sensors can be disabled.

Figure 5:
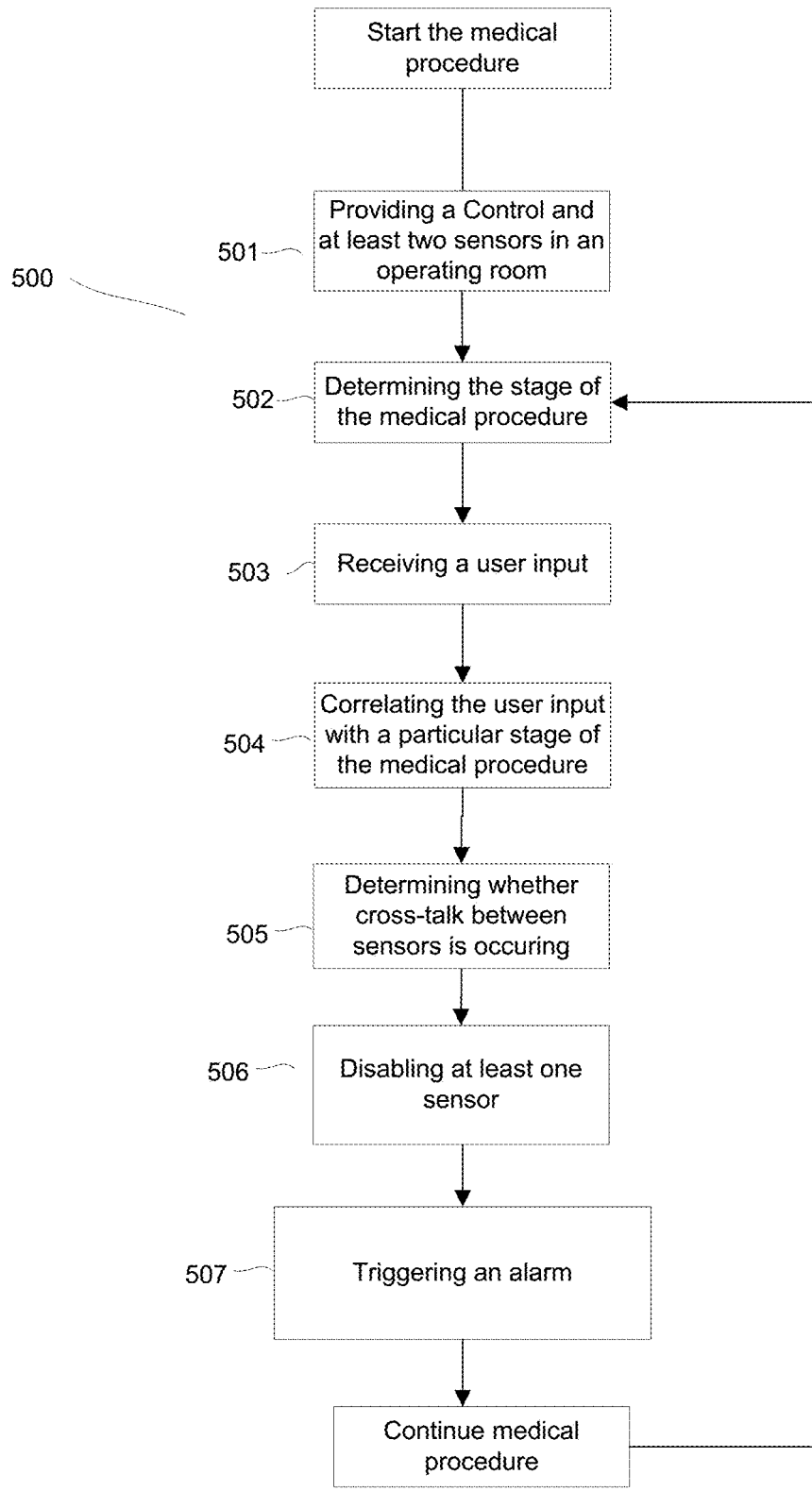
FIG. 5 is a flowchart of an embodiment of the present invention.

Referring to FIG. 5, a cross-talk protocol 500 is provided. Method 500 involves steps for providing a control and at least two sensors 501, determining the stage of a medical procedure 502, receiving a user input 503, correlating the user input with a particular stage of a medical procedure 504, determining whether cross-talk between the sensors is occurring 505, disabling at least one sensor 506, and triggering an alarm 507.

The step of determining whether cross-talk between the sensors involves the control (104, 304) receiving input from both of the sensors. The control then can disable at least one sensor and trigger an alarm. In certain embodiments, the medical procedure is stopped and an error is reported and stored in the processor. In certain embodiments, the detection of a cross-talk situation is handled by applying a set of priority rules to determine whether one or both of the inputs can be safely interpreted and executed. For example, the priority rules may choose only one of the input depending on the priority assigned to the corresponding target device, or based on the quality of the input according to some confidence measurement, or based on the most appropriate action to execute in the particular stage of the medical procedure.

In certain embodiments, the invention also provides additional user feedback to indicate possible interactions and to confirm executed actions. For example, when the surgeon points his/her hand to the surgical monitor, an unobtrusive overlay may be shown to indicate the possible gestures or voice commands. Then, when the surgeon starts a video recording, a corresponding "recording" overlay is shown, and/or a computer voice confirms by saying "video recording started".

In certain embodiments, the system provides reminders to a user to improve the workflow and/or the patient's safety during a medical operation. In certain embodiments, the system automatically and adaptively learns the preferred settings for each of the medical steps of a medical procedure. In certain embodiments, the preferred settings for each of the medical steps of a medical procedure vary depending upon the user, such as a surgeon or nurse that is in the operating room. In certain embodiments, the preferred settings for each user and/or operating team can be stored in a database. In certain embodiments, the control (104, 304) and/or processor (100, 300) store the preferred settings and a prompt is issued at the beginning of the medical procedure in order to determine the medical team performing the surgery, so that the medical team can perform the medical procedure using their preferred settings.

Also, in certain contexts or procedural stages, the cross-talk handling can be considered a hazard mitigation measure. In certain embodiments, the cross-talk handling is performed by a hazard mitigation module.

IV. Operating Room Design

In certain embodiments of the invention, the invention decreases clutter in a surgical operating room. In certain embodiments, the workflow support system automatically detects and identifies individual surgical phases and/or tasks.

In certain embodiments, the system allows for increased simplification of man-machine interface by eliminating some of the multitude of similar control devices (e.g., camera head buttons, footswitches, etc.).

In certain embodiments, the software executing on the processor is able to automatically navigate the IOR through the various settings that are required for each phase or task. For example, the system detects when transitioning from minimally invasive surgery to open surgery and the system configures the instruments for an open surgery by reconfiguring the buttons on the medical devices for the open surgery.

In certain embodiments, use of the medical devices provides input to the workflow support system, which in turn controls the data displayed on the one or more display monitors.

In certain embodiments, a medical device (e.g. camera head with buttons) performs different functions depending upon the phase of the medical procedure. The controls on the medical device functionality are changed based at least in part upon the step of the medical procedure.

Other embodiments of the operating room design include providing various medical devices in the operating room including a camera control unit ("CCU"), various cameras and camera units in communication with the CCU and the processor. In certain embodiments, use of the cameras can control the clinical information provided to the display.

In certain embodiments, the at least one medical device sends data packets to the processor to indicate that the medical device is in use. In certain embodiments, the system uses data from medical devices to identify steps and/or phases of the surgery. For example, once a valve to pump gas is actuated in an insufflation unit, the system knows that insufflation will begin shortly and the relevant data is displayed on the display pertaining to insufflation in a patient.

In certain embodiments, the surgical workflow support system is in communication with the devices in the OR, and can thus send appropriate instructions to the CCU to program the functions associated to the camera buttons.

In certain embodiments, the operating room has multiple displays and sensors associated with each display, as well as sensors associated with various medical devices in the operating room. In this manner, each device has a sensor associated with it, which allows for the devices to communicate with the control to interpret user input, thus, allowing for an operating room design that is less cluttered and allows for a central control to control all of these devices in the operating room.

V. Computer System

Figure 6:
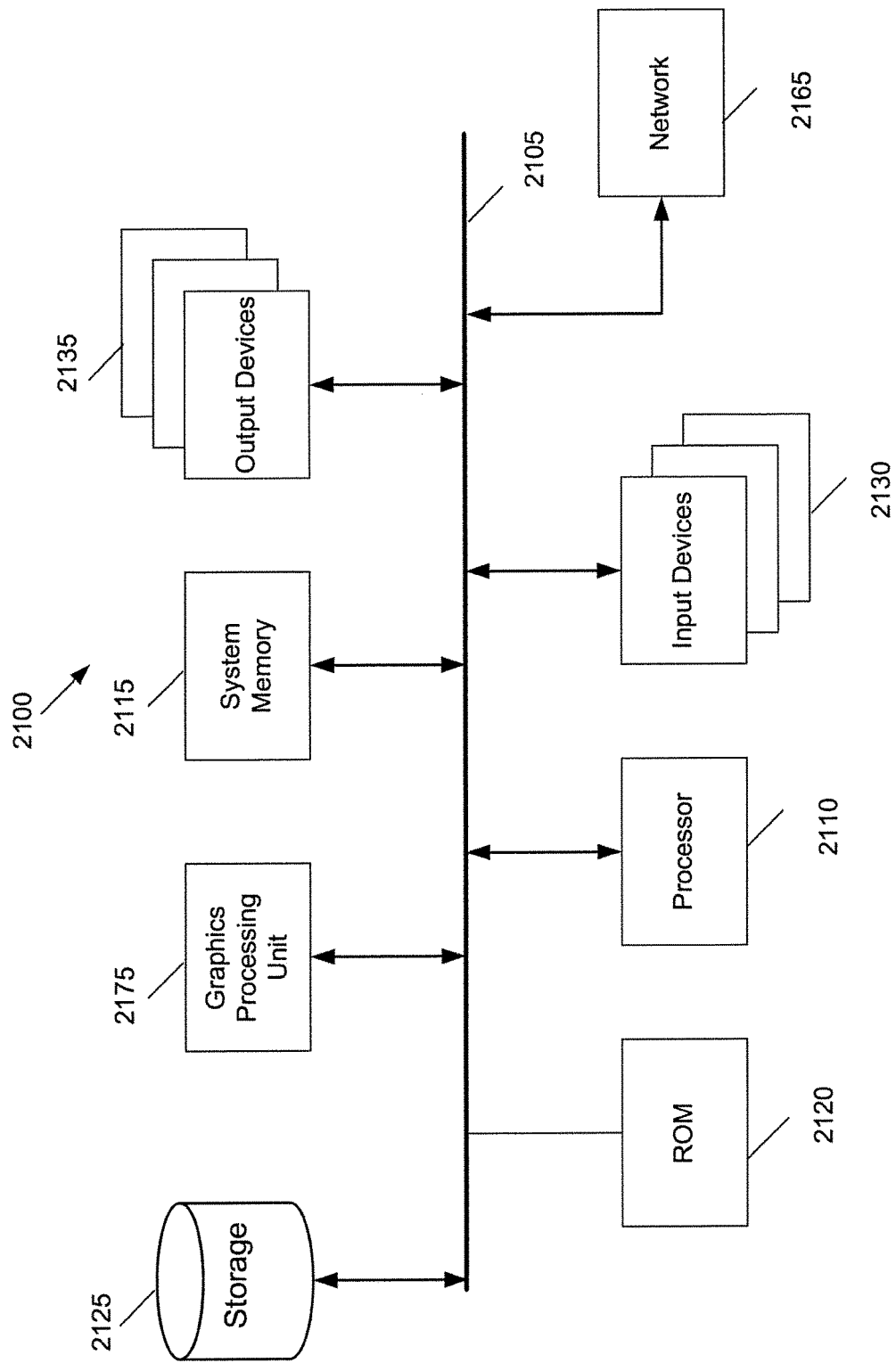
FIG. 6 is a schematic of a computer system that supports the embodiments shown in FIGS. 1-5.

FIG. 6 conceptually illustrates a computer system with which some embodiments of the invention are implemented. The computer system 2100 includes a bus 2105, a processor 2110, a system memory 2115, a read-only memory 2120, a permanent storage device 2125, input devices 2130, and output devices 2135. In some embodiments, the computer system also includes a graphic processing unit (GPU) 2175.

The bus 2105 collectively represents all system, peripheral, and chipset buses that support communication among internal devices of the computer system 2100. For instance, the bus 2105 communicatively connects the processor 2110 with the read-only memory 2120, the system memory 2115, and the permanent storage device 2125.

From these various memory units, the processor 2110 (also referred to as central processing unit or CPU) retrieves instructions to execute and data to process in order to execute the processes of the invention. The read-only-memory (ROM) 2120 stores static data and instructions that are needed by the processor 2110 and other modules of the computer system.

The permanent storage device 2125, on the other hand, is a read-and-write memory device. This device is a non-volatile memory unit that stores instruction and data even when the computer system 2100 is off. Some embodiments of the invention use a mass-storage device (such as a magnetic or optical disk and its corresponding disk drive) as the permanent storage device 2125. The permanent storage device 2125 may be a fully solid-state storage, a conventional "spinning magnetic pallet" storage (i.e. hard-drive), or combinations thereof.

Other embodiments may use a removable storage device (such as a USB flash drive or SD Memory Card) as a temporary storage or as the permanent storage device 2125.

Like the permanent storage device 2125, the system memory 2115 is a read and write memory device. However, unlike storage device 2125, the system memory is a volatile read-and-write memory, such as a random access memory. The system memory stores at least some of the instructions and data that the processor needs at runtime.

Instructions and/or data needed to perform processes of some embodiments are stored in the system memory 2115, the permanent storage device 2125, the read-only memory 2120, or any combination of the three. For example, the various memory units may contain instructions for processing multimedia items in accordance with some embodiments. From these various memory units, the processor 2110 retrieves instructions to execute and data to process in order to execute the processes of some embodiments.

The bus 2105 also connects to the input and output devices 2130 and 2135. The input devices enable the user to communicate information and select commands to the computer system. The input devices 2130 may include alphanumeric keyboards, touch panels, cursors, controllers, and the like. The input devices 2130 may also include scanners through which an image can be input to the computer system. The output devices 2135 display images generated by the computer system. The output devices may include printers, pen plotters, laser printers, ink-jet plotters, film recorders, and display devices, such as cathode ray tubes (CRT), liquid crystal displays (LCD), electroluminescent displays, and the like.

As shown in FIG. 6, bus 2105 also couples computer 2100 to a network 2165 through a network adapter (not shown). In this manner, the computer can be a part of a network of computers (such as a local area network ("LAN"), a wide area network ("WAN"), or an Intranet) or a network of networks (such as the Internet). Finally, as shown in FIG. 6, the computer system in some embodiments also optionally includes a graphics processing unit (GPU) 2175. A GPU (also referred to as a visual processing unit or a display processor) is a dedicated graphics rendering device which is very efficient in manipulating and displaying computer graphics. The GPU can be included in a video card (not shown) or can be integrated into the mother board of the computer system along with the processor 2110. Also, the computer system 2100 may be used as a personal computer, a workstation, a game console, or the like. Any or all of the components of computer system 2100 may be used in conjunction with the invention. However, one of ordinary skill in the art will appreciate that any other system configuration may also be used in conjunction with the invention.

While the invention has been specifically described in connection with certain specific embodiments thereof, it is to be understood that this is by way of illustration and not of limitation and that various changes and modifications in form and details may be made thereto, and the scope of the appended claims should be construed as broadly as the prior art will permit.

The description of the invention is merely exemplary in nature, and thus, variations that do not depart from the gist of the invention are intended to be within the scope of the invention. Such variations are not to be regarded as a departure from the spirit and scope of the invention.

What is claimed is:

1. A system for managing workflow of a medical procedure, the system comprising:
   a control including a control processor, the control able to manipulate a plurality of medical devices in the system via control commands, the control processor tracking the workflow of the medical procedure, including tracking particular stages of the medical procedure based at least in part on data received from the plurality of medical devices;
   at least one detector, the at least one detector able to detect a user input during the medical procedure, the at least one detector being in communication with the control processor;
   wherein the control processor interprets the data signal from the user input according to the particular stage of the medical procedure to determine at least one control command;
   wherein during a first stage of the medical procedure, the user input corresponds to a first command determined by the control processor, and during a second stage of the medical procedure, the user input corresponds to a second command determined by the control processor, the first command different from the second command based at least in part upon the particular stage of the medical procedure;
   wherein the control processor sends the at least one control command to a medical device of the plurality of medical devices to manipulate the medical device, the medical device determined based at least in part upon the at least one control command.

2. The system of claim 1, further comprising:
   a database storing clinical information;
   at least one display monitor displaying a user interface; and
   software executing on said processor for displaying a subset of the clinical information on said at least one display monitor via the interface.

3. The system of claim 2, wherein a different subset of the clinical information is displayed on the at least one display monitor for each stage of the medical procedure, the medical procedure being a multi-stage medical procedure.

4. The system of claim 2, wherein the control is aware of the subset of the clinical information displayed on the interface of said at least one display monitor and interprets the at least one control command based at least in part upon the user input, the clinical information displayed on the interface and the particular stage of the medical procedure.

5. The system of claim 2, wherein the at least one medical instrument manipulated by the control is the at least one display monitor.

6. The system of claim 1, wherein the workflow of the medical procedure is controlled at least in part by the control.

7. The system of claim 1, wherein the medical device includes at least one medical device control, wherein the at least one medical device control performs a different task during different stages of the multi-stage medical procedure.

8. The system of claim 7, wherein the at least one medical device control is able to be reprogrammed to perform a different task during different stages of the multi-stage medical procedure.

9. The system of claim 1, further comprising an image recognition module able to detect a stage of the medical procedure to at least partially determine a subset of clinical information that is displayed on at least one display monitor.

10. The system of claim 1, wherein the user input is gesture control.

11. The system of claim 1, further comprising a hazard mitigation module.

12. The system of claim 11, wherein the hazard mitigation module filters out user input that are not appropriate in the particular stage of the medical procedure.

13. The system of claim 2, wherein during the medical procedure, the control updates the progress of the medical procedure by providing updates through the at least one display monitor.

14. The system of claim 2, wherein the clinical information is divided into subsets according to the authorization level or permission level of an intended recipient of the clinical information.

15. The system of claim 14, wherein a first of the at least one display monitor displays a subset of information that is relevant for a first intended recipient, and wherein a second of the at least one display monitor displays a subset of information that is relevant for a second intended recipient.

16. A method for managing workflow of a medical procedure, the method comprising:
providing a control including a control processor, the control able to manipulate a plurality of medical devices in the system via control commands, the control tracking the workflow of the medical procedure based at least in part on data received from the plurality of medical devices, whereby the workflow of the medical procedure occurs in particular stages;
providing at least one detector, the at least one detector able to detect a user input during the medical procedure, the at least one detector being in communication with the control processor;
receiving a user input during a particular stage of the medical procedure;
correlating the user input with a particular stage of the medical procedure;
determining at least one control command to send to a medical device of the plurality of medical devices;
such that during a first stage of the medical procedure, the user input corresponds to a first command, and during a second stage of the medical procedure, the user input corresponds to a second command, the first command different from the second command based at least in part upon the particular stage of the medical procedure; and
sending the at least one control command to a medical device of the plurality of medical devices to manipulate the medical device, the medical device determined based at least in part upon the at least one control command.

17. The method of claim 16, further comprising:
providing a database storing clinical information;
providing at least one display monitor having an interface; and
providing software executing on said processor for displaying a subset of the clinical information on said at least one display monitor via the interface.

18. The method of claim 17, wherein a different subset of the clinical information is displayed on the at least one display monitor for each stage of a multi-stage medical procedure.

19. The method of claim 17, wherein the control is aware of the subset of the clinical information displayed on said at least one display monitor via the interface and interprets the at least one control command based at least in part upon the user input, the clinical information displayed on said at least one display via the interface and based at least in part on the particular stage of the medical procedure.

20. The method of claim 17, wherein the clinical information displayed on said at least one display monitor is for a multi-stage medical procedure.

21. The method of claim 16, wherein the medical device is an input device that can be dynamically re-programmed.

22. The method of claim 16, wherein the user input is speech recognition and/or gesture control.

23. A system for managing workflow of a medical procedure, the system comprising:
a control including a control processor, the control able to manipulate a plurality of medical devices in the system via control commands, the control processor tracking the workflow of the medical procedure based at least in part on data received from the plurality of medical devices, whereby the workflow of the medical procedure occurs in particular stages;
at least one detector, the at least one detector able to detect a user input during the medical procedure, the at least one detector being in communication with the control processor;
wherein the at least one detector receives a user input and transmits a data signal to the control processor;
wherein the control processor interprets the data signal from the user input to determine at least one control command to send to a medical device of the plurality of medical devices, the medical device determined based at least in part upon the at least one control command;
such that during a first stage of the medical procedure, the user input corresponds to a first command determined by the control processor, and during a second stage of the medical procedure, the user input corresponds to a second command determined by the control processor, the first command different from the second command based at least in part upon the particular stage of the medical procedure.

24. The system of claim 23, wherein the detector is a multi-modal sensor.

25. The system of claim 24, wherein the multi-modal sensor is able to detect a second user input, the second user input being of a different modality than the user input.

26. The system of claim 23, wherein the controller is configured to send the at least one control command to at least two medical devices, the at least one control command being able to control the at least two medical devices.

27. The system of claim 23, further comprising a hazard mitigation module, the hazard mitigation module being able to mitigate errors in interpreting the user input.

28. The system of claim 1, wherein the stages of the medical procedure comprise a pre-operative stage and an operative stage.

* * * * *